(12) United States Patent
Limer et al.

(10) Patent No.: US 10,813,876 B2
(45) Date of Patent: Oct. 27, 2020

(54) PROCESS FOR PREPARING A SILICONE ELASTOMER WITH HYDROPHILIC ACTIVES AND A PERSONAL CARE COMPOSITION CONTAINING THE ELASTOMER

(71) Applicant: Conopco, Inc., Englewood Cliffs, NJ (US)

(72) Inventors: Adam John Limer, Northwich (GB); Anjing Lou, Seymour, CT (US); Brian John Dobkowski, Milford, CT (US); Wei Zhao, Shanghai (CN); Wenhui Song, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 142 days.

(21) Appl. No.: 16/078,720

(22) PCT Filed: Feb. 22, 2017

(86) PCT No.: PCT/EP2017/054062
§ 371 (c)(1),
(2) Date: Aug. 22, 2018

(87) PCT Pub. No.: WO2017/144531
PCT Pub. Date: Aug. 31, 2017

(65) Prior Publication Data
US 2019/0060211 A1 Feb. 28, 2019

(30) Foreign Application Priority Data
Feb. 25, 2016 (WO) ................ PCT/CN2016/074541

(51) Int. Cl.
| | |
|---|---|
| *C08K 5/56* | (2006.01) |
| *A61K 8/895* | (2006.01) |
| *A61K 8/34* | (2006.01) |
| *A61K 8/891* | (2006.01) |
| *A61Q 19/00* | (2006.01) |
| *C08L 83/04* | (2006.01) |
| *A61K 8/06* | (2006.01) |
| *A61Q 19/08* | (2006.01) |
| *C08G 77/12* | (2006.01) |
| *C08G 77/20* | (2006.01) |

(52) U.S. Cl.
CPC ............. *A61K 8/895* (2013.01); *A61K 8/062* (2013.01); *A61K 8/345* (2013.01); *A61K 8/891* (2013.01); *A61Q 19/00* (2013.01); *A61Q 19/08* (2013.01); *C08L 83/04* (2013.01); *A61K 2800/56* (2013.01); *A61K 2800/95* (2013.01); *C08G 77/12* (2013.01); *C08G 77/20* (2013.01)

(58) Field of Classification Search
CPC ........ A61K 8/895; A61K 8/345; A61K 8/891; A61K 8/062; A61Q 19/00; A61Q 19/08
See application file for complete search history.

(56) References Cited

U.S. PATENT DOCUMENTS

| | | | |
|---|---|---|---|
| 2,702,276 A * | 2/1955 | Green .................. | C07F 7/0838 252/8.62 |
| 6,126,925 A | 3/2000 | Bonda et al. | |
| 6,168,782 B1 * | 1/2001 | Lin ........................ | A61K 8/894 424/401 |
| 6,207,717 B1 | 3/2001 | Lin et al. | |
| 6,774,179 B2 | 10/2004 | Ferritto et al. | |
| 8,465,729 B2 | 6/2013 | Dueva et al. | |
| 2003/0165452 A1 | 9/2003 | Gonzalez et al. | |
| 2005/0027051 A1 | 2/2005 | O'Brien et al. | |
| 2007/0142575 A1 | 6/2007 | Zheng et al. | |
| 2007/0148244 A1 | 6/2007 | Kunzler et al. | |
| 2007/0244213 A1 | 10/2007 | Wallace | |
| 2008/0199526 A1 | 8/2008 | Poschalko et al. | |
| 2008/0226708 A1 * | 9/2008 | Lin ......................... | A61K 8/14 424/450 |
| 2009/0028809 A1 | 1/2009 | Cetti et al. | |
| 2013/0230474 A1 * | 9/2013 | Tanner ................... | A61K 8/062 424/60 |
| 2015/0225507 A1 | 8/2015 | Debaugnies et al. | |
| 2018/0179340 A1 * | 6/2018 | Skov ........................ | C08J 3/095 |
| 2019/0055364 A1 | 2/2019 | Limer et al. | |

FOREIGN PATENT DOCUMENTS

| | | |
|---|---|---|
| FR | 2848878 | 6/2004 |
| WO | WO2013162738 | 10/2013 |
| WO | WO2016188885 | 1/2016 |

OTHER PUBLICATIONS

IPRP2 in PCTEP2017054062; dated Jun. 1, 2018.
Search Report & Written Opinion in EP16164095; dated Aug. 2, 2016; European Patent Office (EPO).
Search Report and Written Opinion in EP16164094; dated Aug. 1, 2016.
Search Report and Written Opinion in PCTEP2017054061; dated Apr. 20, 2017.
Search Report and Written Opinion in PCTEP2017054062; dated Apr. 20, 2017.
Written Opinion 2 in PCTEP2017054061; dated Feb. 16, 2018.
Written Opinion 2 in PCTEP2017054062; date Feb. 13, 2018.

* cited by examiner

*Primary Examiner* — Margaret G Moore
(74) *Attorney, Agent, or Firm* — Edward A. Squillante, Jr.

(57) ABSTRACT

A method for preparing silicone elastomers containing hydrophilic skin actives with excellent characteristics is described. The elastomer shows enhanced efficacy with respect to the skin actives compared to skin care compositions formulated with individual elastomer and active components. Skin care compositions containing the inventive silicone elastomers and methods of skin treatment are also described.

11 Claims, No Drawings

PROCESS FOR PREPARING A SILICONE ELASTOMER WITH HYDROPHILIC ACTIVES AND A PERSONAL CARE COMPOSITION CONTAINING THE ELASTOMER

FIELD OF THE INVENTION

The present invention is directed to the polymerization of silicone elastomer and the in-situ entrapment of hydrophilic skin actives within the resulting elastomer. The invention is also directed to the elastomer produced as well as personal care compositions comprising such elastomers whereby the compositions display excellent stability and active performance when compared to formulations traditionally made with hydrophilic active added via batch techniques.

BACKGROUND OF THE INVENTION

Skin, for example, is subject to deterioration through dermatological disorders, environmental abuse (wind, air conditioning, central heating) or through the normal aging process (chronoaging) which may be accelerated by exposure of skin to sun (photoaging). In recent years the demand for personal care compositions and methods for improving the appearance and condition of skin has grown enormously.

It is well known, for example, that presently used hydrophilic actives, like, glycerine, tend to yield poor skin sensory attributes (such as stickiness) when formulated into end use compositions. Other water soluble actives, like vitamins and sunscreens, can interact with other ingredients causing a decrease in formulation stability. Unfortunately, such issues can lead to situations where the cosmetic composition activity is dramatically reduced either during storage or after being applied topically to consumers. Many efforts have been made to improve active efficacy, like sunscreen photostability, by replacing conventional actives with other less effective agents or the addition of active enhancers. However, these methods often result in formulation cost increase and/or a decrease in active efficiency and consumer perceived sensory benefits.

It is of increasing interest to develop ways to stabilize personal care compositions with water soluble actives while simultaneously yielding formulae that result in excellent sensory and active benefits after topical application to skin.

This invention, therefore, is directed to the in-situ entrainment or entrapment of hydrophilic active within a silicone elastomer and during polymerization of the same. The active entrapped elastomer of the present invention is found to improve active stability largely when the active entrapped elastomer is incorporated into end use personal care compositions, especially when comparing such end use compositions with similar compositions to which hydrophilic active has been added in a traditional procedure as a bulk ingredient. The unexpected benefits of the present invention are end use personal care compositions, like skin care compositions, that provide superior active efficacy and excellent sensory benefits resulting from active being contained in elastomer both during and after formulating such personal care compositions.

Additional Information

Efforts have been made to enhance active stability by using different approaches. For example, conventional sunscreen actives have been replaced with less effective agents or combined with SPF enhancers as described in U.S. Pat. Nos. 8,465,729 and 6,126,925, respectively.

Still other efforts have been made to improve active stability by encapsulating the actives in a core shell or structured system. For example, U.S. Pat. No. 6,774,179 discloses a method for entrapping actives in core-shell or gel particles to increase active stability in formulations.

Even further, in U.S. Published Patent Application 2008/0199526, disclosed is a method to encapsulate a primary sunscreen in a microcapsule to enhance the sunscreen stability.

In U.S. Published Patent Application 2009/0028809A1, personal care articles with distinct dispensing zones are described in order to avoid product mixing.

While efforts have been made to enhance active efficiency, none of such efforts are free of results that include poor sensory and/or formulation instability as well as expensive packaging. Moreover, none of such efforts describe a method and composition as claimed in this invention.

SUMMARY OF THE INVENTION

In a first aspect, the present invention is directed to a method for making a silicone elastomer with entrapped hydrophilic active comprising the steps of:
1. combining, in no particular order to produce an unpolymerized mixture of elastomer precursor comprising oil continuous emulsion:
   (i) 0.05 to 8% by weight of a hydride functionalized silicone elastomer precursor;
   (ii) 2 to 60% by weight of a vinyl functionalized silicone elastomer precursor;
   (iii) 0.5 to 97% by weight of a solvent;
   (iv) 0.25 to 65% by weight emulsifier having an HLB from 3 to 12; and
   (v) 0.25 to 60% by weight hydrophilic active, the hydrophilic active forming the internal phase of the oil continuous emulsion; and
2. adding to the unpolymerized mixture comprising oil continuous emulsion catalyst at an amount effective to catalyze polymerization of the hydride and vinyl functionalized elastomer precursors; and
3. recovering silicone elastomer with entrapped hydrophilic active wherein:
   (i) the silicone elastomer produced entraps hydrophilic active and solvent as oil continuous emulsion;
   (ii) at least 20% of total solvent used to make the silicone elastomer is provided before polymerization is initiated; and
   (iii) from 10 to 50% by weight of the total solvent used is provided with the oil continuous emulsion comprising hydrophilic active.

In a second aspect, the present invention is directed to the silicone elastomer made in the first aspect of the invention.

In a third aspect, the present invention is directed to an end use personal care composition comprising the silicone elastomer of the second aspect of this invention.

In a fourth aspect, the present invention is directed to a method or use of the personal care composition of the third aspect of this invention to treat hair, nails and/or skin.

All other aspects of the present invention will more readily become apparent upon considering the detailed description and examples which follow.

Skin, as used herein, is meant to include skin on the face, neck, chest, back, arms (including underarms), hands, legs, buttocks and scalp. Hair includes hair on the head, and nails include both nails on the feet and hands. Hydrophilic active, as used herein, is meant to include a component that improves a body characteristic after topical application like a skin, hair and/or nail characteristic and/or benefits the same wherein the same can be, and preferably, is an active in a leave-on composition, and most preferably, a cream, lotion, balm, deodorant, or gel as well as a shampoo, conditioner or personal wash composition, including a liquid or solid wash composition. Solvent means a hydrophobic material which is a fluid at room temperature and suitable to form the continuous phase of an oil continuous emulsion. Silicone elastomer with entrapped active means silicone elastomer that is cross-linked and has entrapped hydrophilic active in an oil continuous emulsion where solvent makes up the external phase. Therefore, such a silicone elastomer comprises dispersed hydrophilic active present in the internal phase of an oil continuous emulsion and the elastomer has homogeneously dispersed hydrophilic active that is present in an inverted emulsion. In an especially preferred embodiment, the elastomer comprises hydrophilic active that appears as droplet. Hydrophilic active means a water soluble liquid or flowable substance like glycerine and including water wherein hydrophilic active can be pure liquid, a mixture of liquids and liquid having water soluble active dissolved therein, like vitamins and sunscreens.

Hydride functionalized elastomer precursor and vinyl functionalized elastomer precursor may also be referred to as hydride precursor and vinyl precursor, respectively. Comprising as used herein, is meant to include consisting essentially of and consisting of. The silicone elastomer of this invention may, therefore, consist essentially of the polymerization product of hydride functionalized silicone elastomer precursor and vinyl functionalized silicone elastomer precursor, hydrophilic active (within emulsion) and solvent. For the avoidance of doubt, the precursors of the silicone elastomers made in this invention do not comprise oxygen to oxygen bonds, the resulting silicone elastomers with entrapped active and solvent are non-emulsifying elastomers and entrapped hydrophilic active means entrapped in silicone elastomer while in the internal phase of an oil continuous emulsion. Active means a material that provides a benefit when used by a consumer. Emulsion, as used herein, means oil continuous when the same carries hydrophilic active for entrapment into silicone elastomer. In the case of end use product, emulsion includes water-in-oil, oil-in-water or double emulsions. Oil-in-water emulsions are typically preferred end use compositions. All ranges identified herein are meant to include all ranges subsumed therein if, for example, reference to the same is not explicitly made.

Except in the operating and comparative examples, or where otherwise explicitly indicated, all numbers in this description indicating amounts or ratios of materials or conditions or reaction, physical properties of materials and/or use are to be understood as modified by the word "about".

All percentages in the specification and examples are intended to be by weight unless stated otherwise.

DETAILED DESCRIPTION OF THE PREFERRED EMBODIMENTS

The only limitations with respect to the hydride functionalized silicone elastomer precursors suitable for use in this invention are that the same polymerize with the vinyl functionalized elastomer precursors selected for use.

In a preferred embodiment, the hydride functionalized elastomer precursor suitable for use in this invention comprise as blocks or randomly dispersed therein at least one backbone unit of the formulae:

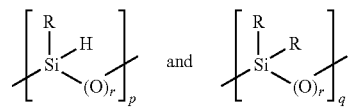

and terminal groups of the formulae:

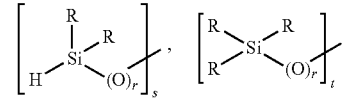

wherein: each R is independently a $C_{1-6}$ alkyl or aryl (preferably a methyl group);
    each r is 0 when the backbone terminates with oxygen and 1 when the backbone terminates with silicon;
    p is 0 to 50, q is 0 to 250, s is 0 to 2, t is 0 to 2, s+t=2, p and s are not simultaneously 0, p+q≥1 and p+s is at least 2 (preferably 2 to 15, and most preferably, 3 to 10).

In an often preferred embodiment, p is 2 to 40, and preferably, 10-30, including all ranges subsumed therein. In another often preferred embodiment, q is 2 to 200, and preferably, 15 to 160, including all ranges subsumed therein.

The only limitation with respect to the vinyl functionalized silicone elastomer precursors suitable for use in this invention is that the same polymerize with the hydride functionalized elastomer precursors selected for use.

In a preferred embodiment, the vinyl functionalized elastomer precursors suitable for use in this invention comprise as blocks or randomly dispersed therein at least one backbone unit of the formulae:

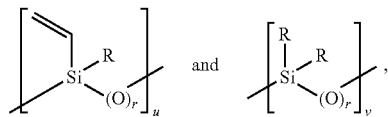

and terminal groups of the formulae:

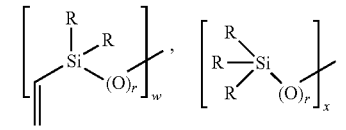

wherein: each R and r are as previously defined, u is 0 to 50, v is 0 to 2,500, w is 0 to 2, x is 0 to 2, w+x=2, u and w are not simultaneously 0, u+v≥1 and u+w is at least 2 (preferably 2 to 15, and most preferably, 2 to 10).

In an often preferred embodiment, u is 0 to 40, and preferably, 0 to 30, including all ranges subsumed therein. In yet another often preferred embodiment, v is 5 to 2250, and preferably, 30 to 1750, including all ranges subsumed therein.

Illustrative examples of the hydride functionalized silicone elastomer precursors that may be used in this invention include Andisil® XL-12, XL-13 and XL-15 (AB Specialty Chemicals) as well as HMS-301 made available from Gelest, Inc. or the like. Illustrative examples of the vinyl functionalized silicone elastomer precursors that may be used in this invention include Andisil VS-6, VS-10, VS-20, VS-50, VS-100, VS-200, VS-250 (AB Specialty Chemicals) as well as DMS-V21 made available from Gelest, Inc. or the like.

Typically, when making the silicone elastomer with entrapped hydrophilic active as described in this invention, the weight ratio of hydride functionalized silicone elastomer precursor (hf) to vinyl functionalized silicone elastomer precursor (vf) is greater than 0.015, and preferably, greater than 0.025, and most preferably from 0.035 to about 0.75, including all ranges subsumed therein. In an often desired embodiment, the ratio of hf/vf is from 0.045 to 0.5, including all ranges subsumed therein.

In another desired embodiment, from 0.05 to 6%, and preferably, from 0.1 to 5%, and most preferably, from 0.1 to 4% by weight hydride functionalized silicone elastomer precursor is used in the method (and product) of this invention based on total weight of hydride precursor, vinyl precursor, active in emulsion, solvent and catalyst used to make the silicone elastomer with entrapped hydrophilic active, including all ranges subsumed therein.

In yet another desired embodiment, from 5 to 50%, and preferably, from 6 to 40%, and most preferably, from 10 to 25% by weight vinyl functionalized silicone elastomer precursor is used in the method (and product) of this invention based on total weight of hydride precursor, vinyl precursor, active in emulsion, solvent and catalyst used to make the silicone elastomer with entrapped hydrophilic active, including all ranges subsumed therein.

The solvent suitable for use in this invention may also be used to make emulsion (i.e., oil-based emulsifying solvent) with hydrophilic active and as the cosmetically acceptable carriers suitable for use in end use compositions that comprise the silicone elastomers with entrapped hydrophilic active of this invention. Such solvent/carriers may include mineral oils, silicone oils, synthetic or natural esters, and alcohols. In the end use compositions amounts of these materials may range from 0.1 to 50%, and preferably, from 0.1 to 30%, and most preferably, from 1 to 20% by weight of the composition, including all ranges subsumed therein. In the silicone elastomer made according to this invention, solvent typically makes up from 1 to 96%, and preferably, 2 to 80%, and most preferably, from 3 to 75% by weight of the total weight of the silicone elastomer with entrapped hydrophilic active, including all ranges subsumed therein. In an especially desired embodiment from 30 to 70% by weight solvent is used based on total weight of the silicone elastomer with entrapped hydrophilic active, including all ranges subsumed therein. For the avoidance of doubt, in the addition/vinyl polymerization carried out to make the silicone elastomer with entrapped active of this invention, solvent is also entrapped with the active in the oil continuous emulsion in the resulting elastomer.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities of less than about 5 centistokes at 25° C. while cyclic materials typically have viscosities of less than about 10 centistokes.

Nonvolatile silicone oils useful as carrier material that are distinct from the reactants used to synthesize inventive elastomer polymer include polyalkyl siloxanes, polyalky-laryl siloxanes, aryl modified silicones (especially phenyl modified di- and trimethicones) and polyether siloxane copolymers. The essentially non-volatile polyalkyl siloxanes useful herein include, for example, polydimethylsiloxanes (like dimethicone) with viscosities of from about 5 to about 100,000 centistokes at 25° C. (under 200 centistokes for elastomer formation). Silicone oils (especially, Dimethicones like C6 to C22 alkyl dimethicone) suitable for use are often made commercially available from Dow Corning are preferred.

Among suitable esters are:
(1) Alkenyl or alkyl esters of fatty acids having 6 to 30 carbon atoms like isopropyl palmitate, isopropyl isostearate, isononyl isonanonoate, oleyl myristate, isopropyl myristate, oleyl stearate, and oleyl oleate;
(2) Ether-esters such as fatty acid esters of ethoxylated fatty alcohols;
(3) Ethers including $C_6$ to $C_{30}$ ethers like dicaprylyl ether; and
(4) Sterol esters, of which soya sterol and cholesterol fatty acid esters are examples thereof.

Often preferred solvents are polydimethylsiloxane (like Cyclo(D5) DC245 as well as Xiameter X-200, 5cst, both made commercially available from Dow Corning), cyclodimethylsiloxane, di and/or trimethicones, dicaprylyl ether or blends or mixtures thereof. To the extent such solvents are modified, they are typically phenyl group modified and/or modified with $C_6$ to $C_{30}$, and preferably, with $C_6$ to $C_{22}$ alkyl groups. Particularly preferred for use as a solvent is caprylyl trimethicone like Silsoft 034 made commercially available from Momentive.

Regarding the hydrophilic actives suitable to be embedded in the silicone elastomers (while in the internal phase of an oil continuous emulsion) made according to this invention, the same are limited only to the extent that they are soluble in the internal phase of an oil continuous emulsion that is embedded in the silicone elastomer making procedure of this invention.

Illustrative examples of the hydrophilic actives suitable for use to embed in the elastomers (via an oil continuous emulsion) include niacinamide, ascorbic and salicylic acids as well as their water soluble derivatives, water soluble extracts like pomegranate extract, dihydroxyacetone, glycerinee, sorbitol, and sunscreens including benzophenone-4, and phenylbenzimidazole sulphonic acid.

The oil continuous emulsion comprising hydrophilic active that is liquid will comprise from 0.5 to 60%, and preferably, from 5 to 60%, and most preferably, from 10 to 55% by weight hydrophilic active, based on total weight of the oil continuous emulsion comprising hydrophilic active and including all ranges subsumed therein.

In the case of hydrophilic actives that are not liquid or fluid but that require oil immiscible liquid like glycerinee and/or water (to be dissolved in and which will then become the internal phase of the oil continuous emulsion with solid hydrophilic active dissolved therein and preferably made prior to combining active with hydride and vinyl precursors), these types of actives typically make up from 0.5 to about 25%, and preferably, from 5 to about 18%, and most preferably, from 6 to 12% by weight of the oil continuous emulsion comprising hydrophilic active, including all ranges subsumed therein.

When making the oil continuous emulsion comprising hydrophilic active, typically the internal phase makes up from 0.5 to 60%, and preferably, from 5 to 60%, and most preferably, from 10 to 55% by weight of the total weight of the oil continuous emulsion and including all ranges subsumed therein.

When making the oil continuous emulsion comprising hydrophilic active, typically from 0.2 to 10%, and preferably, from 0.5 to 8%, and most preferably from 0.75 to 4% by weight emulsifier is used, based on total weight of the oil continuous emulsion and including all ranges subsumed therein.

The emulsifiers preferred for use include those having an HLB from 3 to 12, and preferably, from 4 to 11, and most preferably, from 5 to 8, including all ranges subsumed therein.

Illustrative examples of the preferred emulsifiers suitable for use in making the oil continuous emulsion comprising hydrophilic active include dimethicone having substituents with 8 to 18 ethylene oxide units like PEG-10, PEGH-12 and PEG-14. Others include those with 8-18 propylene glycol units such as PPG-10 and PPG-12. Dimethicone copolyols like PEG-15/PPG-10 and the like may also be used.

In another preferred embodiment, from 10 to 50%, and preferably, from 15 to 35%, and most preferably, from about 16 to 27% of all solvent used in the end use composition described herein comes from solvent that is used to make the oil continuous emulsion comprising hydrophilic active and that is embedded in silicone elastomer of this invention.

The catalyst suitable for use in this invention preferably is a transition metal catalyst like vanadium Oxide, iron, manganese oxide and especially platinum catalysts like Platinum (0)-1,3-divinyl-1,1,3,3-tetramethyldisiloxane. Such a catalyst is limited only to the extent that it enhances polymerization of the hydride and vinyl precursors described herein. Typically, an effective amount of catalyst is used to enhance polymerization. Preferably, from 0.0001 to 0.02% catalyst is used, and most preferably, from 0.0001 to 0.004% by weight catalyst is used, based on total weight of the precursors, solvent, active and catalyst and including all ranges subsumed therein.

In the end use composition comprising the silicone elastomer with entrapped active, typically such composition comprises from 0.001 to 65%, preferably from 0.01 to 35%, and most preferably, from 2 to 30% by weight silicone elastomer with entrapped active, based on total weight of the end use composition and including all ranges subsumed therein.

In another preferred embodiment silicone elastomer is made when moderate mixing/shear (without spilling, shear rates <2000 s$^{-1}$ and with homogenization) is provided under conditions of atmospheric pressure at 15 to 75° C. (preferably 25 to 50° C.). In an especially preferred embodiment, hydrophilic active is added dropwise (0.03 to 0.15 mL, preferably 0.04 to 1 mL) in a time frame from 10 seconds to 10 minutes, and preferably, from 30 seconds to 7 minutes, and most preferably, from 1 minute to 3 minutes including all ranges subsumed therein.

The end use personal care composition comprising the silicone elastomer with embedded active of this invention typically comprises from 0.001 to 95% by weight water, and preferably, from 3 to 85% by weight and most preferably from 10 to 75% by weight water based on total weight of the end use composition and including all ranges subsumed therein.

Distinct from the emulsifiers used in the oil continuous emulsion comprising hydrophilic active, emulsifiers are preferably present in the end use composition containing the inventive elastomer of the present invention. Total concentration of the emulsifier may range from 0.1 to 12%, and preferably, from 1 to 9%, and most preferably, from 1 to 6% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof. Emulsion stabilizers generally classified as vegetable based liquids may also be used in the end use compositions. Preferred stabilizers are sold under the name Oilwax LC and made available commercially by Lotioncrafter.

Preservatives can desirably be incorporated into the end use compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the personal care composition and possible incompatibilities between the preservatives and other ingredients in the emulsion. Preservatives are preferably employed in amounts ranging from about 0.01% to about 2% by weight of the composition, including all ranges subsumed therein.

Thickening agents may optionally be included in such end use personal care compositions. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes cross-linked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from about 0.001 to about 5%, and preferably, from 0.1 to 3%, and most preferably, from 0.2 to 1.5% by weight of the end use composition including all ranges subsumed therein.

Conventional humectants may be employed in the end use compositions. These are generally polyhydric alcohol-type materials. Typical polyhydric alcohols include glycerine (i.e., glycerinee or glycerine), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerine, propoxylated glycerine and mixtures thereof. Most preferred is glycerine, propylene glycol or a mixture thereof. The amount of humectant employed may range anywhere from 0.5 to 20%, preferably between 1 and 15% by weight of the end use composition.

Fragrances, colorants, fixatives and abrasives may optionally be included in end use compositions of the present invention. Each of these substances may range from 0.05 to 5%, preferably between 0.1 and 3% by weight.

Azelaic acid, ubiquinone, dihydroxyacetone resorcinols like 4-ethyl resorcinol, 4-hexyl resorcinol, 4-phenylethyl resorcinol, 4-cyclopentyl resorcinol, 4-cyclohexyl resorcinol, hydroxyacids, mixtures thereof and the like and mixtures thereof may also be used as actives in the end use composition of this invention apart from the actives in the inventive elastomer. Such compounds, when used either alone or collectively, typically make up from 0.001 to 6%, and preferably, from 0.01 to 5%, and most preferably, from 0.5 to 3.5% by weight of the end use composition, including all ranges subsumed therein.

Desquamation promoters may be present in the end use compositions together with the inventive elastomer. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from 0.01 to 15% by weight of the end use composition.

A variety of herbal extracts may optionally be included in the personal compositions together with the inventive elastomer. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary. Soy extracts may be used and especially when it is desirable to include retinol.

Conventional buffers/pH modifiers may be used apart from the inventive elastomer and in the end use compositions of this invention. These include commonly employed additives like sodium hydroxide, potassium hydroxide, hydrochloric acid, citric acid and citrate/citric acid buffers.

In an especially preferred embodiment, the pH of the end use composition of this invention is from 4 to 8, and preferably, from 4.25 to 7.75, and most preferably, from 5.5 to 7.5, including all ranges subsumed therein. (The end use composition of this invention may be a solid stick or bar.) Viscosity of the end use composition of this invention is, however, preferably from 1,000 to 120,000 cps, and most preferably, from 5,000 to 80,000 cps taken at ambient temperature and a shear rate of 1 $s^{-1}$ with a strain controlled parallel plate rheometer made commercially available from suppliers like T.A. Instruments under the Ares name.

When making the silicone elastomers with entrapped hydrophilic actives, in no particular order and before polymerization begins, hydride precursor, vinyl precursor, solvent and emulsifier are combined. Hydrophilic active is preferably added last in the manner previously described. Greater than 20% by weight of the total amount of solvent, and preferably, from 50 to 85%, and most preferably, from 55 to 75% by weight of the total amount of solvent (including all ranges subsumed therein) should be added initially and until polymerization is almost completed after catalyst addition (i.e., 90 to 99% of the hydride precursor being polymerized). Subsequent to polymerization being almost complete, the remainder of solvent should be added gradually and typically within 5 to 30 minutes, and preferably, within 8 to 26 minutes, and most preferably, within 10 to 20 minutes so that the resulting silicone elastomer with entrapped hydrophilic active has a viscosity from 50 to 3,000 cps, and preferably from about 100 to 2,000 cps, and most preferably, from 500 to about 1,600 cps, including all ranges subsumed therein where viscosity is determined with a strain controlled parallel plate rheometer as previously described.

The temperature at which the polymerization reaction takes place ranges from 15 to 75° C., and preferably, from 20 to 70° C., and most preferably from 30 to 65° C., including all ranges subsumed therein.

Surprisingly, the silicone elastomer with entrapped hydrophilic active of the present invention is stable for three days, preferably 5 days, and most preferably, for at least 7 days after being stored at 40° C. where stable is defined to mean remaining homogeneous, at least translucent (slightly turbid, and deplete of visual separation and active droplet formation). The same is also not tacky or sticky to touch even when the hydrophilic active is glycerinee.

The silicone elastomer of the present invention has a G' storage module from 700 to 10,000 Pa, and preferably, from 750 to 8,000 Pa, and most preferably, from 775 to 2,500 Pa, including all ranges subsumed therein. In an often desired embodiment, G' storage modules for the silicone elastomers of the present invention is from 800 to 1,500, including all ranges subsumed therein (G' storage modulus obtained by Dynamic Mechanical Analysis, Standard ASTM 4065, parallel plates with 25 mm diameter).

A wide variety of packaging can be employed to store and deliver the end use composition of this invention. Preferably the package should be able to contain or prevent any elevated pressure build-up during storage and use of the product. Pump dispensers configured to either prevent or withstand high pressure build-up, may be used.

Packaging is often dependent upon the type of personal care composition. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

The following examples are provided to facilitate an understanding of the present invention. The examples are not intended to limit the scope of the claims.

Example 1

Elastomer compositions consistent with this invention have been prepared. Active was added before polymerization was initiated.

| Material | Sample 1 | Sample 2 | Sample 3 | Sample 4 | Sample 5 |
| --- | --- | --- | --- | --- | --- |
| Silicone Hydride[1] | 1.03 g | 1.18 g | 1.08 g | 1.04 g | 0.88 g |
| Vinyl Silicone[2] | 12.9 g | 12.79 g | 11.24 g | 9.97 g | 8.62 g |
| Cyclo PDMS (D5) | 64.69 g | 64.87 g | 56.59 g | 50.06 g | 42.52 g |
| Glycerine | 20.0 g | 20.15 g | 29.61 g | 37.07 g | 45.69 g |
| PEG-10 Dimethicone | 1.0 g | 1.01 g | 1.48 g | 1.85 g | 2.29 g |
| Cyclo PDMS (D5)[3] | 29.0 g | 29.0 g | 29.0 g | 29.0 g | 29.0 g |
| Visual appearance at room temperature | Stable invert emulsion | Stable invert emulsion | Stable invert emulsion | Stable invert emulsion | Stable invert emulsion |

[1]AB Silicones, HMS-301, Gelest, Inc. (hydride functionalized silicone elastomer precursor)
[2]AB Silicones, DMS-V21, Gelest, Inc. (vinyl functionalized silicone elastomer precursor)
[3]Solvent added post polymerization, Dow Corning DC245.

Example 1—Preparation of Silicone Elastomer Containing Glycerinee

Sample 1 was made by mixing under conditions of homogenization, oil phase and a mixture of methylhydrosiloxane di-methyl siloxane copolymer (Gelest Inc.—HMS-301, 1.03 g), vinyl terminated polydimethylsiloxane (Gelest Inc.—DMS-V21, 12.9 g), DC245 (Dow Corning, 64.69 g), and PEG-10 dimethicone (Shin Etsu—KF-6017, 1.0 g); glycerine (20.0 g) was added (0.06 mL) dropwise over two minutes. After mixing for approximately 10 minutes, the resulting stable water-in-oil emulsion was transferred into a 250 mL dry round flask, heated at 45° C. for 5 min, and stirred at 200 rpm with an anchor stirrer. 25 uL of the platinum catalyst (Sigma Aldrich, 2% Platinum(0)-1,3-divinyl-1,1,3,3-tetramethyldisiloxane in xylene) was added. In 5-10 minutes a gelled mixture was formed, with stirring continuing at 200 rpm for another 5 hours at 45° C. to ensure a complete reaction. The gel was diluted with additional DC245 (29 g) to reduce the final viscosity of the silicone elastomer with entrapped hydrophilic active.

Samples 2 through 5 were made in a manner similar to one used to make Sample 1 except that the amount of ingredients used varied.

The results and observations for all samples indicated that when active is added prior to polymerization, a stable white and homogeneous elastomer is produced with an invert phase of a hydrophilic active, and the same is not sticky/tacky notwithstanding the fact that glycerine has been added.

Additionally, the product made according to this invention is stable, unexpectedly displaying no phase separation or oil droplet formation after being stored at 45° C. for seven days. Such product is also excellent for use in end use product formation.

Example 2—Preparation of Silicone Elastomer Containing Glycerine

A mixture of methylhydrosiloxane—dimethylsiloxane copolymer (Gelest Inc—HMS-301, 1.04 g), vinyl terminated polydimethylsiloxanes (Gelest Inc—DMS-V21, 12.9 g), and DC245 (Dow Corning, 65.69 g) were charged into a 250 mL dry round flask, heated at 45° C. for 5 min, and stirred at 200 rpm with an anchor stirrer. Added to the flask was 25 uL of the platinum catalyst (Sigma Aldrich, 2% Platinum(0)-1,3-divinyl-1,1,3,3-tetramethyldisiloxane in xylene). In 5-10 minutes a gelled mixture was formed, with stirring continuing at 200 rpm for another 5 hours at 45° C. to ensure a complete reaction. The gel was diluted with further DC245 (28.58 g) to reduce the final viscosity. A mixture of glycerine (20.0 g) and PEG-10 dimethicone (Shin Etsu—KF-6017, 1.0 g) was added with mixing for another 30 minutes. The recovered product is a silicone elastomer with glycerine added post monomer polymerization.

The results and visual observations (after making the sample of Example 2) indicated that when active is added after polymerization, a very cloudy heterogenous elastomer product (with large active droplets) is formed. The elastomer with glycerin added after polymerization was also very sticky/tacky to the touch and difficult to use when formulating end use compositions.

Additionally, the sample of Example 2, when stored at 45° C. for seven days displayed significant phase separation and the internal phase of the product separated as droplets on the product surface.

The invention claimed is:

1. A method for making a silicone elastomer with entrapped active, comprising the steps of:
   1. combining, in no particular order to produce an unpolymerized mixture with oil continuous emulsion:
      (i) 0.05 to 8% by weight of a hydride functionalized silicone elastomer precursor;
      (ii) 2 to 60% by weight of a vinyl functionalized silicone elastomer precursor;
      (iii) 0.5 to 97% by weight of a solvent;
      (iv) 0.25 to 65% by weight emulsifier having an HLB from 3 to 12; and
      (v) 0.25 to 60% by weight hydrophilic active comprising glycerine, the hydrophilic active forming the internal phase of the oil continuous emulsion; and
   2. adding to the unpolymerized mixture with oil continuous emulsion catalyst at an amount effective to catalyze polymerization of the hydride and vinyl functionalized elastomer precursors; and 3. recovering silicone elastomer with entrapped hydrophilic active wherein:
(i) the silicone elastomer produced entraps hydrophilic active comprising glycerine and solvent as oil continuous emulsion;
(ii) at least 20% of total solvent used to make the silicone elastomer is provided before polymerization is initiated; and
(iii) from 10 to 50% by weight of the total solvent used is provided with the oil continuous emulsion comprising hydrophilic active wherein any remainder of solvent used is added gradually within 5 to 30 minutes after 90 to 99% of the hydride precursor has polymerized and the silicone elastomer with entrapped hydrophilic active has a viscosity from 50 to 3000 cps at ambient temperature and a G' storage modulus from 700 to 10,000 PA.

2. The method for making a silicone elastomer according to claim 1 wherein 0.05 to 6% by weight hydride functionalized silicone elastomer precursor is used.

3. The method for making a silicone elastomer according to claim 1 wherein 5 to 50% by weight vinyl functionalized silicone elastomer precursor is used.

4. The method for making a silicone elastomer according to claim 1 wherein the weight ratio of hydride functionalized silicone elastomer precursor to vinyl functionalized silicone elastomer precursor is greater than 0.015.

5. The method for making a silicone elastomer according to claim 1 wherein the method is carried out at a temperature from 15 to 75° C.

6. The method for making a silicone elastomer according to claim 1 wherein the hydride functionalized elastomer precursor comprises at least one backbone unit of the formulae:

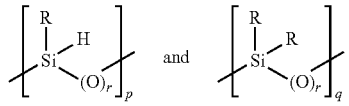

and terminal groups of the formulae:

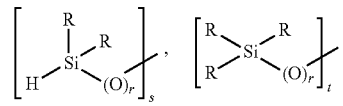

wherein:
a) each R is independently a $C_{1-6}$ alkyl or aryl
b) each r is independently 0 or 1, and r in the terminal group is 0 when r is 1 in the backbone unit and the backbone unit terminates with oxygen and 1 when r is 0 in the backbone unit and the backbone unit terminates with silicon;
c) p is 0 to 450, q is 0 to 250, s is 0 to 2, t is 0 to 2, s+t=2, p and s are not simultaneously 0, p+q≥1 and p+s is at least 2.

7. The method for making a silicone elastomer according to claim 1 wherein the vinyl funcitonalized elastomer precursor comprises as blocks or randomly dispersed therein at least one backbone unit of the fomulae:

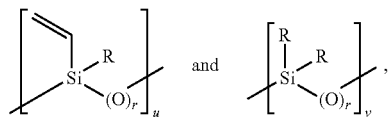

and terminal groups of the formulae:

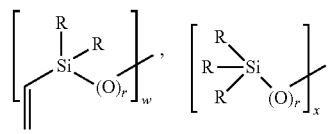

wherein:
a) each R is independently a $C_{1-6}$ alkyl or aryl;
b) each r is independently 0 or 1, and r in the terminal group is 0 when r is 1 on the backbone unit and backbone unit terminates with oxygen and 1 when r is 0 in the backbone unit and the backbone unit terminates with silicon;
c) u is 0 to 50, V is 0 to 2,500, w is 0 to 2, x is 0 to 2, w+x=2, v and w are not simultaneously 0, u+v≥1 and u+w is at least 2.

8. The method for making a silicone elastomer according to claim 1 wherein the solvent comprises a polydimethylsiloxane.

9. A silicone elastomer obtainable by the process of claim 1.

10. An end use composition which is an emulsion comprising from 0.001 to 45% by weight of the silicone elastomer obtainable by the process of claim 1.

11. The composition of claim 10 wherein the composition is used to treat hair, nails and/or skin.

* * * * *